United States Patent
Yamada et al.

(10) Patent No.: US 7,455,641 B2
(45) Date of Patent: Nov. 25, 2008

(54) ULTRASONIC TREATMENT APPARATUS

(75) Inventors: Norihiro Yamada, Tokyo (JP); Haruhiko Ueno, Tokyo (JP); Hiroyuki Takahashi, Tokyo (JP); Hiroyoshi Watanabe, Tokyo (JP); Keita Suzuki, Tokyo (JP); Mitsumasa Okada, Tokyo (JP); Takeaki Nakamura, Tokyo (JP)

(73) Assignee: Olympus Corporation (JP)

( * ) Notice: Subject to any disclaimer, the term of this patent is extended or adjusted under 35 U.S.C. 154(b) by 550 days.

(21) Appl. No.: 10/842,934

(22) Filed: May 10, 2004

(65) Prior Publication Data

US 2005/0027310 A1 Feb. 3, 2005

(30) Foreign Application Priority Data

Jul. 30, 2003 (JP) .............................. 2003-282725

(51) Int. Cl.
*A61B 8/00* (2006.01)
*A61H 1/00* (2006.01)

(52) U.S. Cl. .......................................... 600/437; 601/2
(58) Field of Classification Search ................ 600/437, 600/459, 462; 601/2; 606/113
See application file for complete search history.

(56) References Cited

U.S. PATENT DOCUMENTS

| | | | | |
|---|---|---|---|---|
| 4,732,156 A | * | 3/1988 | Nakamura | ................... 600/445 |
| 6,231,578 B1 | | 5/2001 | Rajhansa | .................... 606/113 |
| 6,328,703 B1 | * | 12/2001 | Murakami | ....................... 601/4 |
| 6,681,783 B2 | * | 1/2004 | Kawazoe | ................ 134/169 C |
| 2003/0225332 A1 | | 12/2003 | Okada et al. | |
| 2006/0247558 A1 | * | 11/2006 | Yamada | ......................... 601/2 |

FOREIGN PATENT DOCUMENTS

| | | |
|---|---|---|
| DE | 44 43 947 | 7/1995 |
| EP | 0 119 614 | 9/1984 |
| EP | 0 668 052 | 8/1995 |
| JP | 60-92224 | 6/1985 |
| JP | 2-124128 | 5/1990 |
| JP | 8-286121 | 11/1996 |
| JP | 11-56867 | 3/1999 |
| JP | 2000-254139 | 9/2000 |

(Continued)

OTHER PUBLICATIONS

Office Action issued by Japanese Patent Office on Jan. 10, 2007 in connection with corresponding Japanese application No. 2003-282725.

(Continued)

*Primary Examiner*—Eric F Winakur
*Assistant Examiner*—Michael T. Rozanski
(74) *Attorney, Agent, or Firm*—Ostrolenk, Faber, Gerb & Soffen, LLP

(57) ABSTRACT

An ultrasonic treatment apparatus comprises an endoscope having an insertion portion to be inserted in a body cavity, and a treatment unit having an ultrasonic vibrator which generates ultrasonic vibrations, and a treatment portion which performs treatment by utilizing the ultrasonic vibrations generated by the ultrasonic vibrator. The ultrasonic treatment apparatus further comprises a treatment unit holding portion, which is provided in a distal end portion of the insertion portion and to which the treatment unit is attached, a cable which transmits an electric signal to the ultrasonic vibrator, and at least one bundle member which bundles the insertion portion and the cable.

7 Claims, 6 Drawing Sheets

FOREIGN PATENT DOCUMENTS

| | | |
|---|---|---|
| JP | 2000-296135 | 10/2000 |
| JP | 2000-342597 | 12/2000 |
| JP | 2001-87266 | 4/2001 |

OTHER PUBLICATIONS

English translation of Japanese Office Action dated Jan. 10, 2007 issued in connection with corresponding Japanese application No. 2003-282725.

Office Action issued by the Japanese Patent Office on Oct. 2, 2007 in connection with corresponding Japanese Patent Application No. 2003-282725.

Translation of the Office Action issued by the Japanese Patent Office on Oct. 2, 2007 in connection with corresponding Japanese Patent Application No. 2003-282725.

* cited by examiner

ULTRASONIC TREATMENT APPARATUS

CROSS-REFERENCE TO RELATED APPLICATIONS

This application is based upon and claims the benefit of priority from prior Japanese Patent Application No. 2003-282725, filed Jul. 30, 2003, the entire contents of which are incorporated herein by reference.

BACKGROUND OF THE INVENTION

1. Field of the Invention

The present invention relates to an ultrasonic treatment apparatus, which treats a target of treatment by ultrasonic vibrations under observation through an endoscope.

2. Description of the Related Art

Conventionally, an ultrasonic treatment apparatus, which treats a target of treatment by ultrasonic vibrations under observation through an endoscope, has been used. For example, U.S. Pat. No. 6,231,578 discloses an ultrasonic treatment apparatus for use with an endoscope. The ultrasonic treatment apparatus for use with an endoscope has a flexible wire inserted through a channel of the endoscope. The distal end of the flexible wire forms a looped treatment portion. The proximal end portion thereof is connected to an ultrasonic vibrator incorporated in an operation unit. When a target is to be treated, the flexible wire is inserted through the channel of the endoscope, and the treatment portion is projected out of the rear end of the endoscope and holds the target. Then, ultrasonic vibrations generated by the ultrasonic vibrator are transmitted to the treatment portion through the flexible wire. The target is treated with the treatment portion, utilizing the transmitted ultrasonic vibrations.

Jpn. Pat. Appln. KOKAI Publication No. 11-56867 discloses an ultrasonic surgical apparatus as an ultrasonic treatment apparatus. In the ultrasonic surgical apparatus, an ultrasonic vibrator is attached to the distal end of a holding rod inserted through a trocar. A blade for performing treatment by means of ultrasonic vibrations is integrally attached to the ultrasonic vibrator to form a treatment unit. When a target is to be treated, the holding rod is inserted in the trocar, so that the treatment unit is inserted in a body cavity. In this state, the target is treated with the blade, utilizing the ultrasonic vibrations generated by the ultrasonic vibrator.

BRIEF SUMMARY OF THE INVENTION

According to an aspect of the present invention, there is provided an ultrasonic treatment apparatus comprising: an endoscope having an insertion portion to be inserted in a body cavity; a treatment unit having an ultrasonic vibrator which generates ultrasonic vibrations, and a treatment portion which performs treatment by utilizing the ultrasonic vibrations generated by the ultrasonic vibrator; a treatment unit holding portion, which is provided in a distal end portion of the insertion portion and to which the treatment unit is attached; a cable which transmits an electric signal to the ultrasonic vibrator; and at least one bundle member which bundles the insertion portion and the cable.

Preferably, the treatment unit holding portion has a vibrator hole, and the ultrasonic vibrator is sealed within the vibrator hole.

Preferably, the treatment unit holding portion is fixed to a node position of the ultrasonic vibrations of the treatment unit.

Preferably, the treatment portion has a distal end portion located at a position a quarter wavelength of the ultrasonic vibrations of the treatment unit apart from the node position.

Preferably, the ultrasonic treatment apparatus further comprises: another treatment unit attached to the treatment unit holding portion and having another ultrasonic vibrator which generates ultrasonic vibrations, and another treatment portion which grasps a target of treatment in cooperation with the treatment portion and performs treatment by utilizing the ultrasonic vibrations generated by the other ultrasonic vibrator; another cable which transmits an electric signal to the other ultrasonic vibrator and is bundled together with the cable and the insertion portion by the at least one bundle member; and an ultrasonic oscillating apparatus to which the cable and the other cable is connected and drives the ultrasonic vibrator and the other ultrasonic vibrator in phases opposite to each other.

Preferably, the ultrasonic vibrator and the other ultrasonic vibrator are driven at frequencies different from each other.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
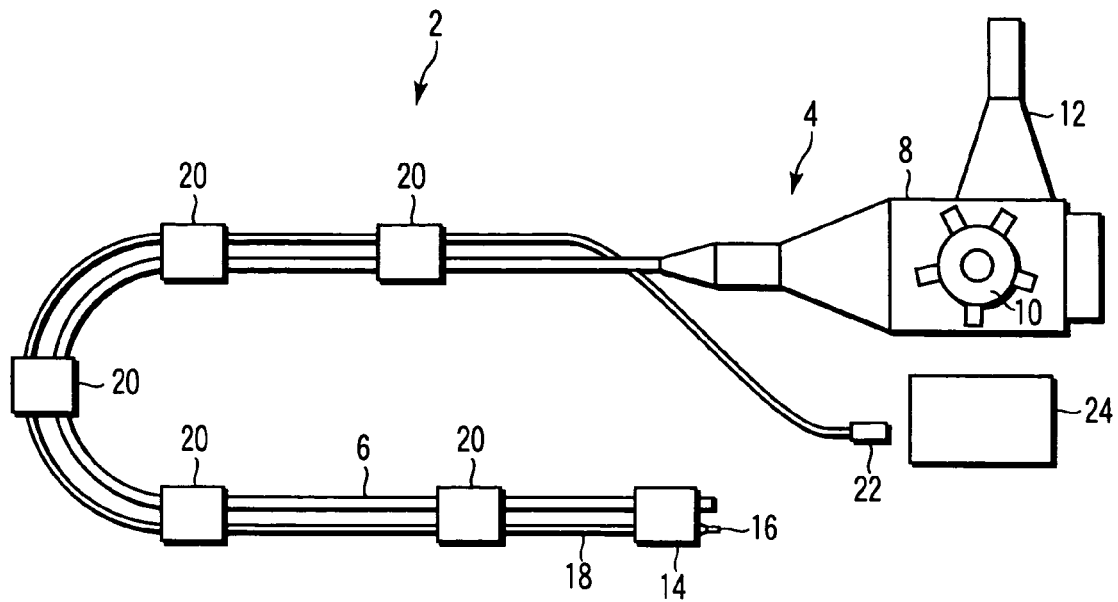
FIG. 1 is an explanatory view showing an ultrasonic treatment apparatus according to a first embodiment of the present invention.

A first embodiment of the present invention will be described with reference to FIGS. 1 to 4. FIG. 1 shows a schematic structure of the whole of an ultrasonic treatment apparatus 2 of the present invention. The ultrasonic treatment apparatus 2 comprises an endoscope 4 to observe a target of treatment. The endoscope 4 has a long insertion portion 6 to be inserted in a body cavity. The proximal end of the insertion portion 6 is connected to a main body 8, which is held by an operator. A bending operation portion 10, to operate the distal end of the insertion portion 6 back and forth and left and right, is disposed on the main body 8. A universal cord 12 extends from the main body 8. An image guide and a light guide (to be described later) are inserted through the universal cord 12.

The endoscope 4 comprises a treatment unit holding portion 14 connected to the distal end of the insertion portion 6. The treatment unit holding portion 14 holds a treatment unit 16, which performs treatment utilizing ultrasonic vibrations.

Figure 2:
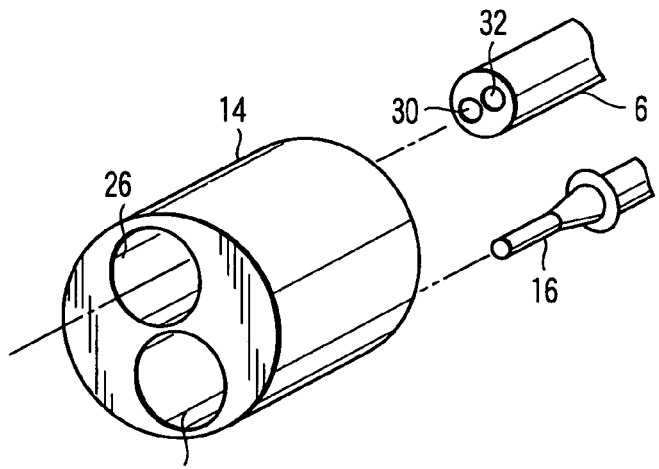
FIG. 2 is an explanatory view showing a distal end portion of the ultrasonic treatment apparatus of the first embodiment.

As shown in FIG. 2, according to this embodiment, the treatment unit holding portion 14 is cylindrical. The treatment unit holding portion 14 has two holes (an insertion portion hole 26 and a vibrator hole 28), which extend in the axial direction. The insertion portion 6 is removably inserted in the insertion portion hole 26. The treatment unit 16 is contained in the vibrator hole 28.

An observation system lens 30 to observe a target is disposed on the distal end portion of the insertion portion 6. An illumination system lens 32 to illuminate the target is arranged adjacent to the observation system lens 30. The observation system lens 30 is connected to the distal end of the image guide inserted through the insertion portion 6, while the illumination system lens 32 is connected to the distal end of the light guide inserted through the insertion portion 6. The image guide and the light guide are inserted through the insertion portion 6, the main body 8 (FIG. 1) and the universal cord 12 (FIG. 1). The rear end of the image guide is connected to a video and the rear end of the light guide is connected to a light source.

Figure 3:
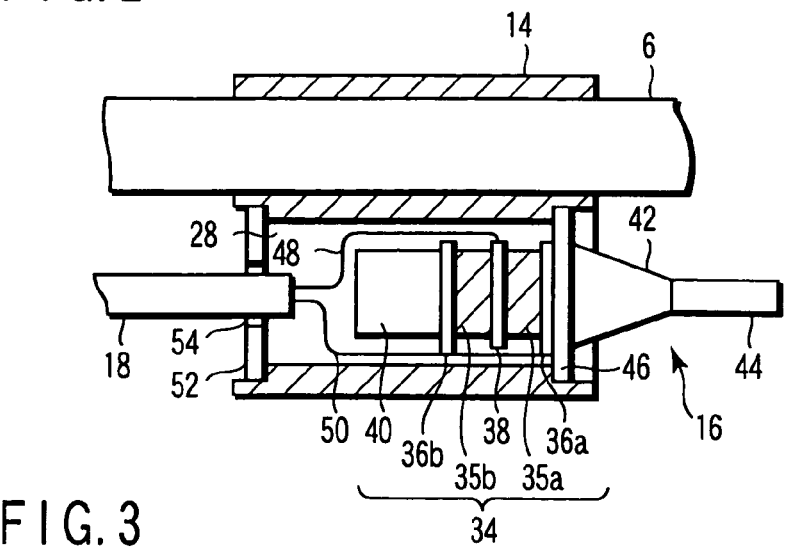
FIG. 3 is a sectional view of a distal end portion of the ultrasonic treatment apparatus of the first embodiment.

As shown in FIG. 3, the treatment unit 16 comprises an ultrasonic vibrator 34, which generates ultrasonic vibrations. The ultrasonic vibrator 34 has a front piezoelectric element 35a and a rear piezoelectric element 35b, disposed adjacent to each other. A positive electrode 38 is interposed between the piezoelectric elements 35a and 35b. Negative electrodes 36a and 36b are respectively disposed on the front end of the piezoelectric element 35a and the rear end of the piezoelectric element 35b. A liner plate 40 made of metal is arranged in the rear end portion of the ultrasonic vibrator 34.

A horn 42, which transmits ultrasonic vibrations, is connected to the distal end of the ultrasonic vibrator 34. A distal end treatment portion 44, which treats the target by using the transmitted ultrasonic vibrations, is formed to the distal end of the horn 42. A flange portion 46 is formed in a proximal end portion of the horn 42. The flange portion 46 is fixed to a step portion formed in the vibrator hole 28 by laser welding. Alternatively, the treatment unit 16 may be fixed to the vibrator hole 28 by another way, for example, by screwing.

The flange portion 46 is located at a node of the ultrasonic vibrations of the treatment unit 16. The distance between the flange portion 46 and the top of the distal end treatment portion 44 is a quarter of the wavelength of the ultrasonic vibrations of the treatment unit 16. Therefore, the top of the distal end treatment portion 44 is located at a loop of the ultrasonic vibrations of the treatment unit 16.

A positive lead 48 and a negative lead 50 are respectively connected to the positive electrode 38 and the negative electrodes 36a and 36b. The positive lead 48 and the negative lead 50 are bundled and coated with an insulator to form a wire cable 18. The wire cable 18 passes through a through hole 54 formed in a partition 52 fixed to the rear end of the vibrator hole 28. The gap between the wire cable 18 and the partition 52 is sealed with silicone or the like. Therefore, all components of the treatment unit 16 except for the horn 42 are isolated from the outside.

Referring back to FIG. 1, the wire cable 18 extends along the insertion portion 6 of the endoscope 4. The insertion portion 6 and the wire cable 18 are bundled by a plurality of bundle members 20. The number of bundle members 20 may be determined in accordance with the length of the insertion portion of the endoscope 4.

A connector 22 is connected to the rear end of the wire cable 18. The connector 22 is detachably connected to an ultrasonic oscillating apparatus 24. Operating means (not shown), such as a foot switch or a hand switch, is connected to the ultrasonic oscillating apparatus 24.

Figure 4:
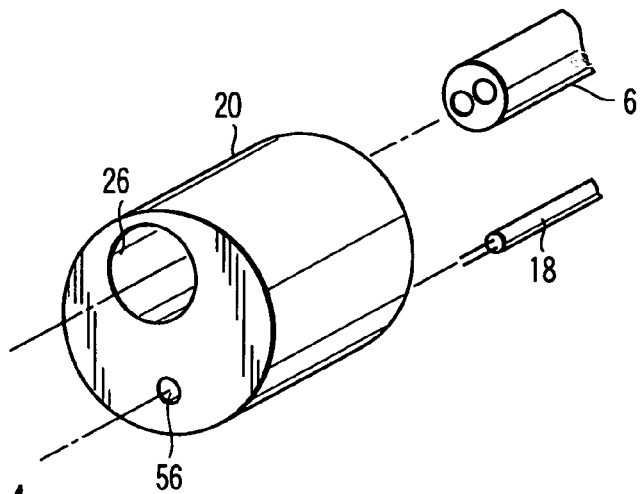
FIG. 4 is an explanatory view showing a bundle member of the ultrasonic treatment apparatus of the first embodiment.

As shown in FIG. 4, the bundle member 20 of this embodiment is cylindrical. The bundle member 20 has two holes (an insertion portion hole 26 and a wiring hole 56), which extend in the axial direction. The insertion portion 6 is removably inserted in the insertion portion hole 26. The wire cable 18 is removably inserted in the wiring hole 56.

An operation of the ultrasonic treatment apparatus 2 of this embodiment will now be described. The insertion portion 6 of the endoscope 4, integral with the treatment unit 16 and the wire cable 18, is inserted into a body cavity. The target is observed in the video through the observation system lens 30, while the illumination system lens 32 is illuminating the target, so that the diseased part is recognized. Thereafter, as the observation is continued, the distal end of the insertion portion 6 is operated back and forth and left and right by operating the bending operation portion 10, thereby moving the treatment unit 16 toward the diseased part. The bending operation portion 10 is further operated, so that the distal end treatment portion 44 can be located at a suitable position of the target of treatment.

The operating means of the ultrasonic oscillating apparatus 24 is operated to generate an electric signal. The generated electric signal is transmitted to the ultrasonic vibrator 34 through the positive lead 48 and the negative lead 50. The ultrasonic vibrator 34 converts the electric signal to mechanical vibrations, thereby generating ultrasonic vibrations. The ultrasonic vibrations are transmitted to the horn 42, and then to the distal end treatment portion 44. The target is subjected to treatment (e.g., as breaking, emulsification or hemostasis) with the distal end treatment portion 44 utilizing the ultrasonic vibrations of the treatment unit 16.

Advantages of the structure described above will now be described. First, according to this embodiment, the treatment unit holding portion 14 integrally holds the distal end portion of the insertion portion 6 of the endoscope 4 and the treatment unit 16, and the bundle member 20 bundles the insertion portion 6 and the wire cable 18. Thus, the endoscope 4, the treatment unit 16 and the wire cable 18 are integral with one another. For this reason, observation by the endoscope and various treatment by the treatment unit, such as cutting or coagulation, can be carried out simultaneously. Moreover, treatment within the body cavity can be performed by low-invasive procedures.

Secondly, all components of the treatment unit 16 except for the horn 42 are isolated from the outside. In other words, the piezoelectric elements 35*a* and 35*b* of the treatment unit 16 inserted in the body cavity are sealed. This is desirable for the patient.

Thirdly, the treatment unit 16 is fixed to the treatment unit holding portion 14 in the flange portion 46 located at a node of the ultrasonic vibrations of the treatment unit 16. Therefore, when the treatment unit 16 is ultrasonically vibrated to treat the target with the treatment unit 16, the loss of the ultrasonic vibrations of the treatment unit 16 is sufficiently small.

Fourthly, the flange portion 46 of the treatment unit 16 fixed to the treatment unit holding portion 14 is located at a node of the ultrasonic vibrations of the treatment unit 16. The distance between the flange portion 46 and the distal end treatment portion 44 is a quarter of the wavelength of the ultrasonic vibrations of the treatment unit 16. In other words, the distal end treatment portion 44 is located at a loop of the ultrasonic vibrations of the treatment unit 16. The loop is closest of all to the flange portion 46. Therefore, the total length of the treatment unit 16 is small.

Figure 5:
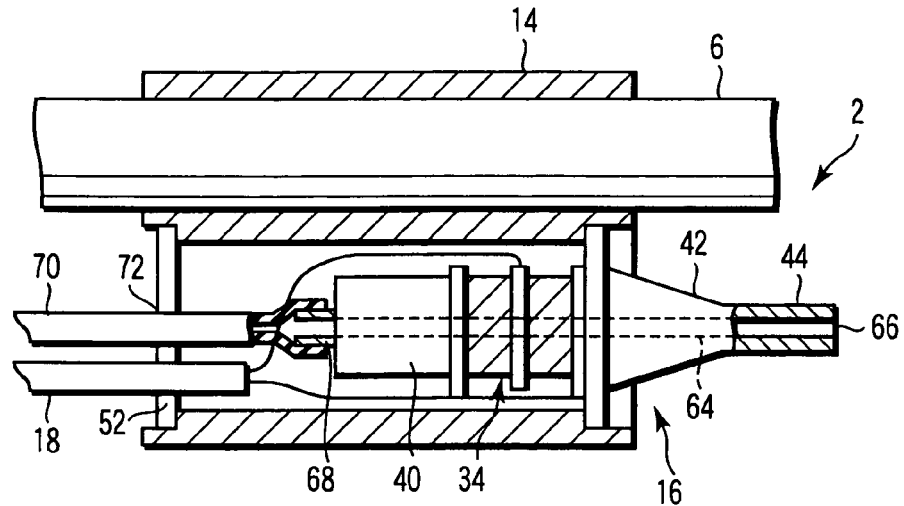
FIG. 5 is a sectional view of a distal end portion of an ultrasonic treatment apparatus according to a second embodiment of the present invention.
Figure 6:
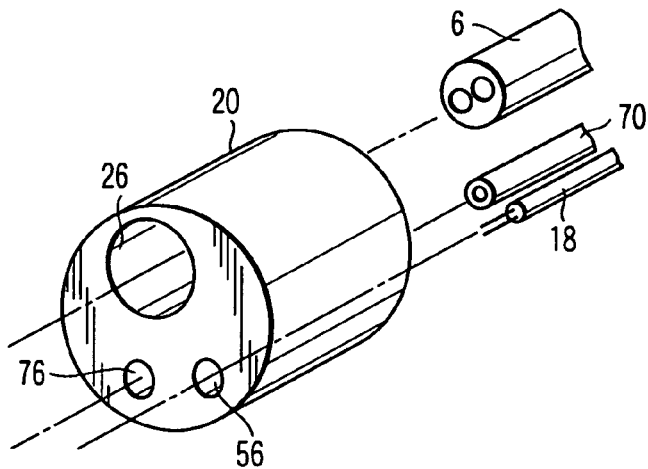
FIG. 6 is an explanatory view showing a bundle member of the ultrasonic treatment apparatus of the second embodiment.
Figure 7:
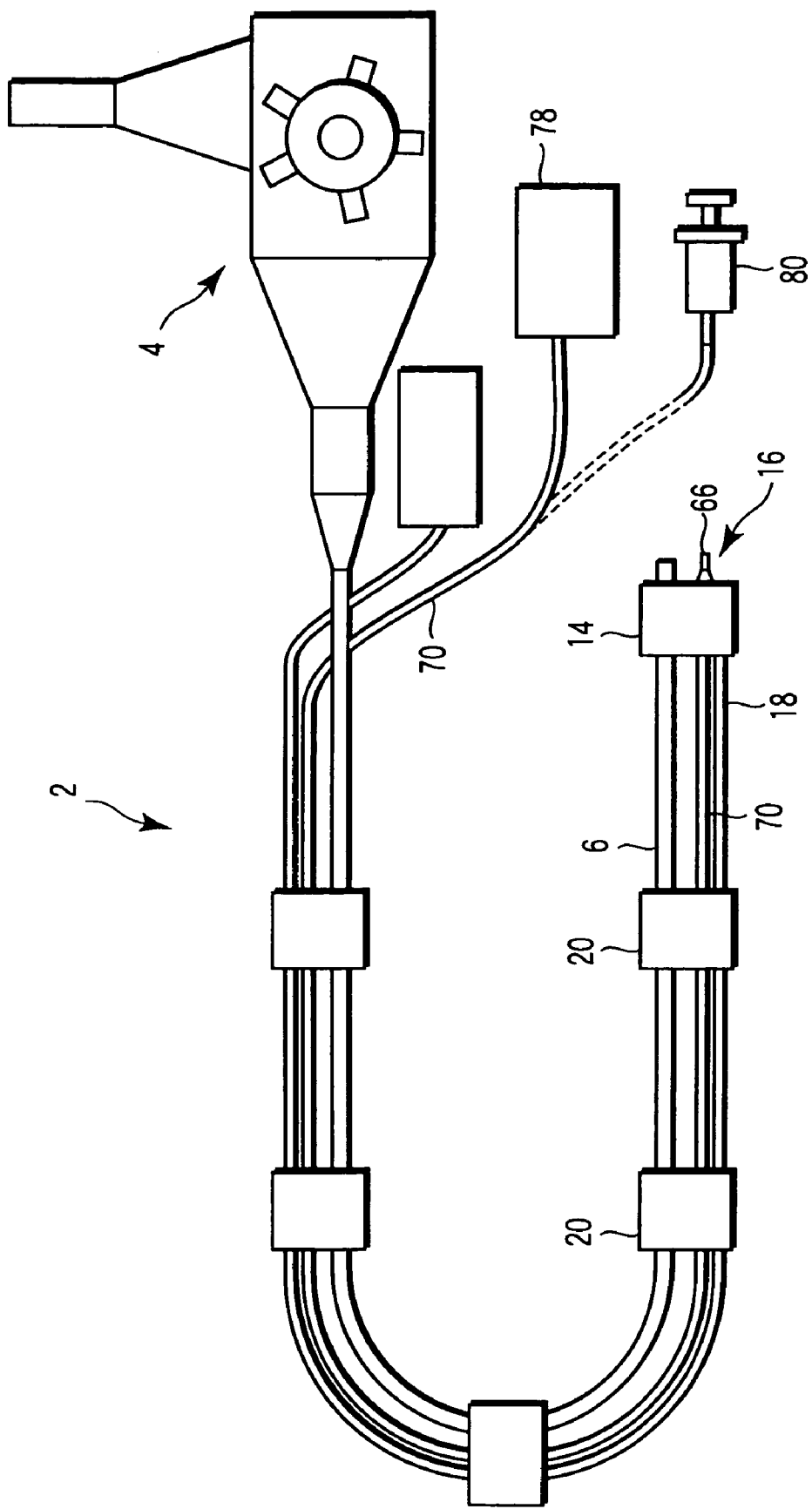
FIG. 7 is an explanatory view showing the ultrasonic treatment apparatus of the second embodiment.

FIGS. 5 to 7 show a second embodiment of the present invention. The same elements as in the first embodiment are identified by the same reference numerals as those used for the first embodiment, and descriptions thereof are omitted. As shown in FIG. 5, the horn 42 and the ultrasonic vibrator 34 of the ultrasonic treatment apparatus 2 have a hollow suction path 64 extending in the axial direction. The distal end of the suction path 64 forms an opening 66 at the top of the distal end treatment portion 44. The rear end portion of the suction path 64 forms a connecting portion 68 projected from the liner plate 40. A flexible suction tube 70 is connected to the connecting portion 68. The flexible suction tube 70 is inserted through a second through hole 72 formed in the partition 52. As in the case of the wire cable 18, the gap between the suction tube 70 and the partition 52 is sealed.

As shown in FIG. 6, the bundle member 20 has a suction tube hole 76 extending in the axial direction along the insertion portion hole 26 and the wiring hole 56. The suction tube 70 is removably inserted in the suction tube hole 76.

As shown in FIG. 7, the rear end of the suction tube 70 is connected to a suction apparatus 78. Alternatively, it is connected to a cylinder 80 filled with a drug.

The operation of the ultrasonic treatment apparatus 2 of this embodiment is basically the same as that of the ultrasonic treatment apparatus 2 of the first embodiment. After the target is subjected to treatment (e.g., breaking, emulsification or hemostasis) with the distal end treatment portion 44, the suction apparatus 78 is operated, so that unnecessary broken or emulsified tissues are sucked and collected through the opening 66 at the top of the distal end treatment portion 44.

When a drug is to be injected into the diseased part, the rear end of the suction tube 70 is connected to the cylinder 80. Then, the opening 66 at the top of the distal end treatment portion 44 is directed to the diseased part, to which the drug should be injected. As the treatment unit 16 is ultrasonically vibrating, the cylinder 80 is pushed, so that the drug is sprayed to the target diseased part from the opening 66 through the suction tube 70 and the suction path 64.

The second embodiment with the above structure has the following advantage in addition to those of the first embodiment. In the second embodiment, the opening 66 formed at the top of the distal end treatment portion 44 is connected to the suction apparatus 78 or the cylinder 80 through the suction path 64 and the suction tube 70. Therefore, unnecessary tissues, broken or emulsified by the distal end treatment portion 44 utilizing the ultrasonic vibrations, can be sucked and collected. In addition, a drug can be sprayed or injected to the diseased part.

Figure 8A:
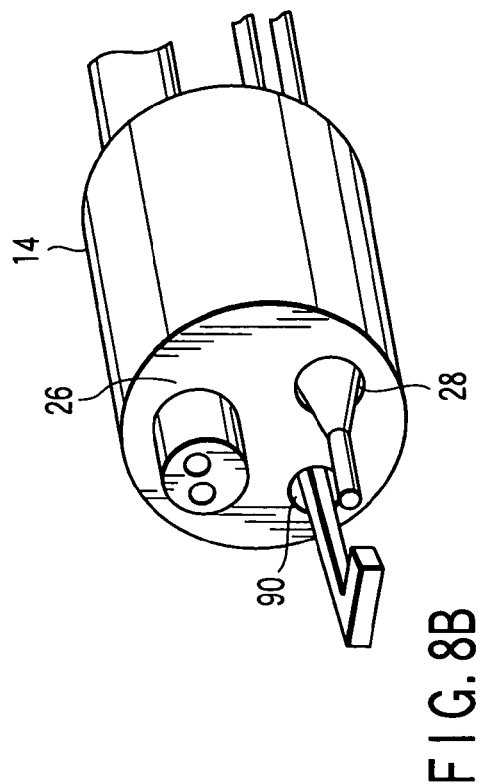
FIG. 8A is a sectional view of a distal end portion of an ultrasonic treatment apparatus according to a third embodiment of the present invention.
Figure 8B:
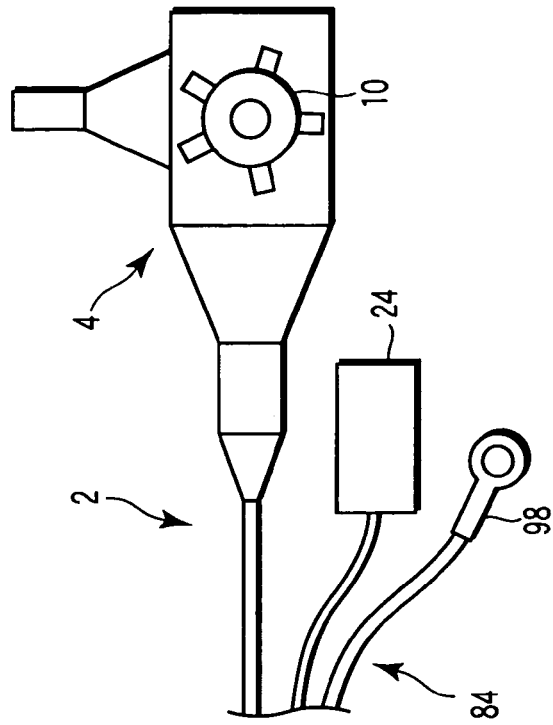
FIG. 8B is an explanatory view showing the distal end portion of the ultrasonic treatment apparatus of the third embodiment.
Figure 8C:
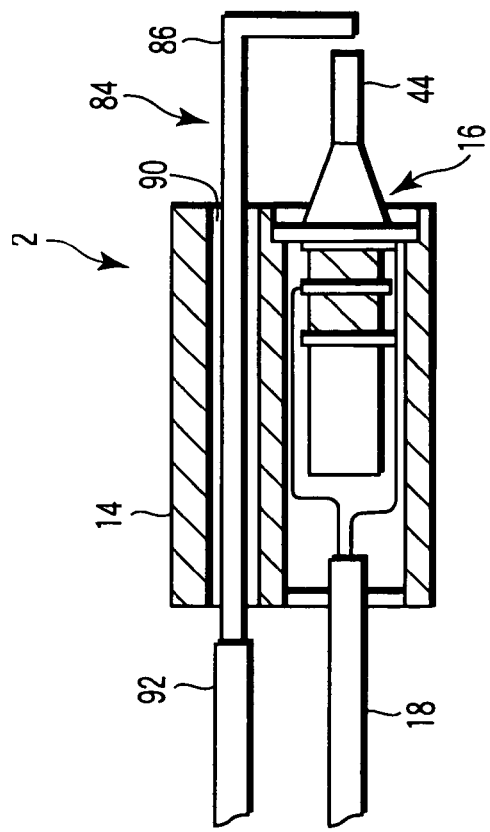
FIG. 8C is an explanatory view showing the ultrasonic treatment apparatus of the third embodiment.

FIGS. 8A to 8C show a third embodiment of the present invention. The same elements as in the first embodiment are identified by the same reference numerals as those used for the first embodiment, and descriptions thereof are omitted. As shown in FIG. 8A, the ultrasonic treatment apparatus 2 of this embodiment has a grasp tool 84, which grasps a target of treatment in cooperation with the distal end treatment portion 44.

The grasp tool 84 has an L-shaped grasp portion 86 in its distal end portion. A first portion, extending along the axial direction of the treatment unit holding portion 14, is formed in a rear end portion of the grasp portion 86. The first portion is movable forward and backward through a grasp tool hole 90 extending along the axial direction of the treatment unit holding portion 14.

A second portion is formed in the distal end portion of the grasp portion 86. The second portion extends from the top end of the first portion toward the distal end treatment portion 44 of the treatment unit 16 along the top end face of the treatment unit holding portion 14. The top end portion of the second portion is aligned in front of the distal end treatment portion 44. The top end portion of the second portion can be brought into contact with the distal end treatment portion 44, by moving the first portion backward relative to the treatment unit holding portion 14 through the grasp tool hole 90. A flexible sheath 92 is connected to the rear end portion of the grasp portion 86.

As shown in FIG. 8B, the grasp tool hole 90 extends in the axial direction of the treatment unit holding portion 14 along the insertion hole 26 and the vibrator hole 28. Referring to FIG. 8C, each of the bundle members 20 has a sheath hole 96 extending in the axial direction of the bundle member 20 along the insertion hole 26 and the vibrator hole 28. The flexible sheath 92 is removably inserted in the sheath hole 96.

An operating portion 98 is arranged at the rear end of the grasp tool 84. The flexible sheath 92 is moved by operating the operating portion 98, so that the first portion of the grasp portion 86 is moved relative to the treatment unit holding portion 14 through the grasp tool hole 90.

An operation of the ultrasonic treatment apparatus 2 of this embodiment will now be described. The operation of the ultrasonic treatment apparatus 2 of this embodiment is basically the same as that of the first embodiment. The bending operation portion 10 is operated under observation through the endoscope 4, so that the distal end treatment portion 44 and the grasp portion 86 can be located at a suitable position of the diseased part to be treated. Then, the operating portion 98 is pulled toward the rear side, thereby moving the first portion of the grasp portion 86 relative to the treatment unit holding portion 14 through the grasp tool hole 90 toward the rear side. As a result, the target of treatment is grasped by the distal end treatment portion 44 and the second portion of the grasp portion 86. Thereafter, the operating means of the ultrasonic oscillating apparatus 24 is operated to ultrasonically vibrate the treatment unit 16. The distal end treatment portion 44 applies various treatments to the target of treatment by utilizing the ultrasonic vibrations.

The third embodiment with the above structure has the following advantage in addition to those of the first embodiment. In the third embodiment, in the state where the target of treatment is grasped by the distal end treatment portion 44 and the grasp portion 86, the grasped target can be treated by the distal end treatment portion 44 utilizing ultrasonic vibrations.

Figures 9A, 9B:
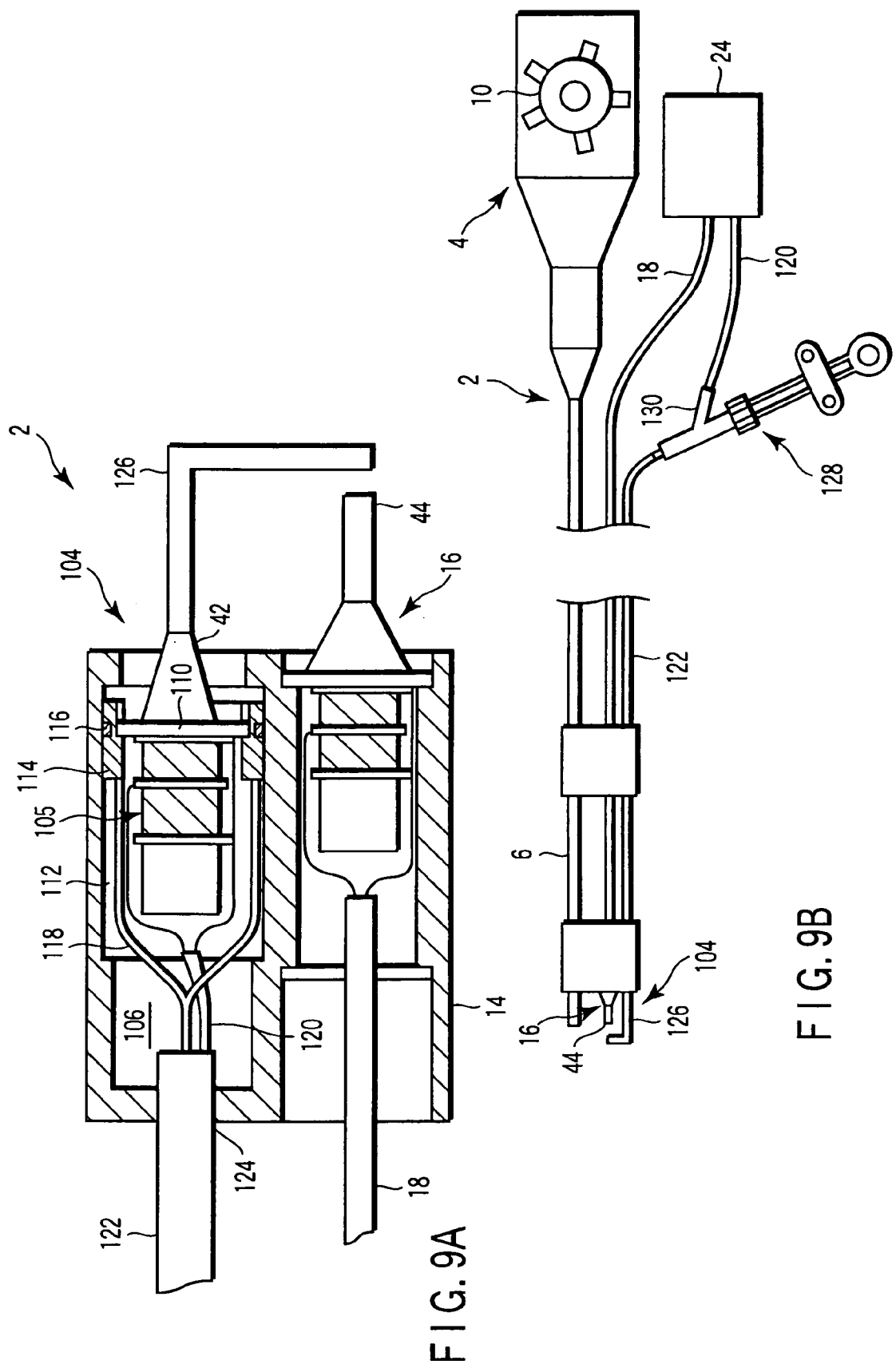
FIG. 9A is a sectional view of a distal end portion of an ultrasonic treatment apparatus according to a fourth embodiment of the present invention.
FIG. 9B is an explanatory view showing the ultrasonic treatment apparatus of the fourth embodiment.
Figure 10:
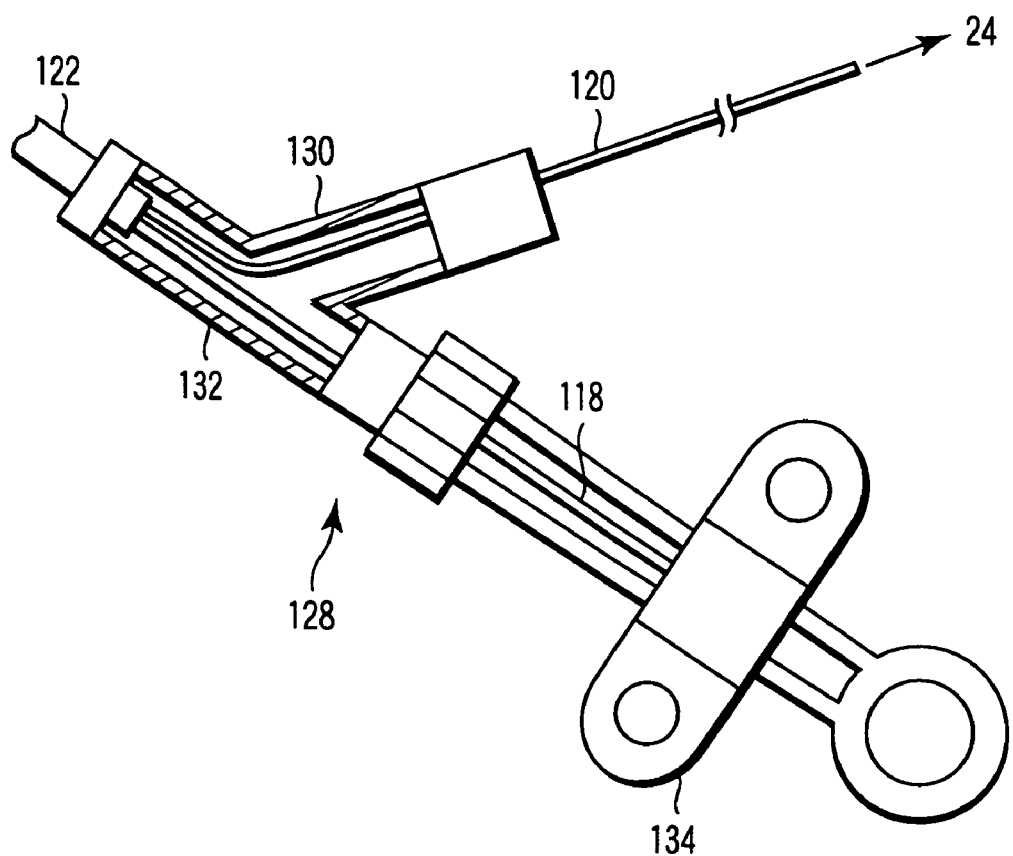
FIG. 10 is an explanatory view showing an operating portion of the ultrasonic treatment apparatus of the fourth embodiment.

FIGS. 9A, 9B and 10 show a fourth embodiment of the present invention. The same elements as in the third embodiment are identified by the same reference numerals as those used for the third embodiment, and descriptions thereof are omitted. As shown in FIG. 9A, the treatment unit 16 having the same structure as that of the third embodiment is disposed in the treatment unit holding portion 14 of the ultrasonic treatment apparatus 2 of this embodiment. The treatment unit 16 is called the first treatment unit 16. The components of the first treatment unit 16, which are the same as those in the third embodiment, are identified by the same terms as those that are used for in the third embodiment with the word "first" at the beginning of each term.

The treatment unit holding portion 14 has a second vibrator hole 106 extending in the axial direction along the first vibrator hole 28 (FIG. 8B) and the insertion portion hole 26 (FIG. 8B). The second vibrator hole 106 contains a second treatment unit 104.

The second treatment unit 104 has a second ultrasonic vibrator 105. The second treatment unit 104 has a distal end treatment portion, which forms a grasp portion 126 of the same form as the distal end side of the grasp portion of the third embodiment. A second flange portion 110 is formed in the proximal end portion of the horn 42 of the second treatment unit 104.

The second vibrator hole 106 has a larger diameter portion 112. A moving member (driving means) 114 is disposed in the larger diameter portion 112. The second flange portion 110 of the second treatment unit 104 is fixed to the moving member 114. In this embodiment, the second flange portion 110 is screwed to the moving member 114 with nuts.

The moving member 114 is substantially cylindrical and coaxial with the larger diameter portion 112. The outer diameter of the moving member 114 is substantially equal to the inner diameter of the larger diameter portion 112. A circumferential groove is formed in the outer circumferential surface of the moving member 114. An O-ring 116 is fitted in the circumferential groove. With this structure, the outer circumferential surface of the moving member 114 is fitted to the inner circumferential surface of the larger diameter portion 112 with friction force acting therebetween, while the inside of the second vibrator hole 106 is kept watertight.

An operation wire 118 to transmit driving force is fixed to the rear end of the moving member 114. More specifically, the top end of the operation wire 118 is divided into two. The two top ends of the operation wire 118 are fixed to the moving member 114 at positions opposing to each other with respect to the central axis of the moving member 114. The operation wire 118 is inserted in a hollow flexible sheath 122 together with a second wire cable 120 of the second treatment unit 104. The flexible sheath 122 passes through a through hole 124 formed in the rear end wall of the treatment unit holding portion 14 at the rear end portion of the second vibrator hole 106. The flexible sheath 122 is fixed to the rear end wall in a watertight manner.

As shown in FIG. 9B, an operating portion 128 is arranged in the rear end portion of the flexible sheath 122. A branched portion 130 is branched from the operating portion 128. The second wire cable 120 extends from the end of the branch portion 130 and is connected to the ultrasonic oscillating apparatus 24. The ultrasonic oscillating apparatus 24 is configured to transmit electrical signals of different frequencies and phases to the first treatment unit 16 and the second treatment unit 104 through the first and second wire cables 18 and 120.

FIG. 10 shows a detailed configuration of the operating portion 128. The flexible sheath 122 is inserted in an opening of the distal end of a cylindrical portion 132 in the distal end portion of the operating portion 128. The second wire cable 120 and the operation wire 118 are drawn out of the flexible sheath 122 within the cylindrical portion 132 in its distal end portion. The second wire cable 120 is inserted in the branched portion 130 and drawn out of the opening at the end of the branched portion 130 as described above.

The operation wire 118 is drawn out of the opening at the rear end of the cylindrical portion 132. The proximal end of the operation wire 118 is fixed to a handle 134 arranged in the rear end portion of the operating portion 128. The handle 134 is slidable relative to the operating portion 128 in the longitudinal direction of the operation wire 118.

An operation of the ultrasonic treatment apparatus 2 of this embodiment will now be described. The operation of the ultrasonic treatment apparatus 2 of this embodiment is basically the same as that of the third embodiment. The bending operation portion 10 is operated so that the distal end treatment portion 44 and the grasp portion 126 can be located at a suitable position of the diseased part to be treated under observation through the endoscope 4. Then, the handle 134 is pulled relative to the operating portion 128, thereby pulling the operation wire 118 toward the rear side. Accordingly, the second treatment unit 104 is moved toward the rear side relative to the treatment unit holding portion 14 along the larger diameter portion 112. As a result, the target of treatment is grasped by the distal end treatment portion 44 and the second portion of the grasp portion 86.

Thereafter, the operating means of the ultrasonic oscillating apparatus 24 is operated to ultrasonically vibrate the first treatment unit 16 and the second treatment unit 104. Various treatments are carried out for the target of treatment by utilizing the ultrasonic vibrations.

At this time, it is possible to drive the first treatment unit 16 and the second treatment unit 104 in the opposite phases by the ultrasonic oscillating apparatus 24. In this case, the distal end treatment portion 44 and the grasp portion 126 repeatedly approach to and separate from each other, thereby treating the grasped portion.

Further, the first treatment unit 16 and the second treatment unit 104 can be driven at different frequencies. In this case, ultrasonic vibrations of the frequency equal to the difference between the frequencies of the distal end treatment portion 44 and the second treatment unit 104 occurs due to a beat in the target of treatment grasped by the distal end treatment portion 44 and the grasp portion 126. The grasped target is treated by the ultrasonic vibrations generated due to the beat.

For example, if the first treatment unit 16 is driven at 200 kHz and the second treatment unit 104 is driven at 170 kHz, ultrasonic vibrations at 30 kHz due to a beet occur in the target of treatment grasped by the distal end treatment portion 44 and the grasp portion 126.

The fourth embodiment with the above structure has the following advantage in addition to those of the third embodiment. In the fourth embodiment, the target of treatment is grasped by the distal end treatment portion 44 of the first treatment unit 16 and the grasp portion 126 of the second treatment unit 104. In this state, the grasped target can be treated by the distal end treatment portion 44 and the grasp portion 126 utilizing the ultrasonic vibrations of the first treatment unit 16 and the second treatment unit 104.

At this time, it is possible to drive the first treatment unit 16 and the second treatment unit 104 in the opposite phases. In this case, the distal end treatment portion 44 and the grasp portion 126 repeatedly approach to and separate from each other, thereby treating the grasped portion. Therefore, the treatment capability can be higher than that in the case where one treatment unit carries out the treatment. Consequently, the target can be treated more quickly.

The first and second treatment units 16 and 104 must be small enough to be used in the body cavity together with the endoscope 4. Thus, since the lengths of the first and second treatment units 16 and 104 are restricted, the frequency of the ultrasonic vibrations determined by the lengths of first and second treatment units 16 and 104 is inevitably as high as 100 kHz or higher. However, to treat a hard target, such as a calculus, it is desirable that the frequency of the ultrasonic vibrations be 50 kHz or lower.

According to this embodiment, the first treatment unit 16 and the second treatment unit 104 can be driven at different frequencies. In this case, ultrasonic vibrations of the frequency equal to the difference between the frequencies of the two units occur due to a beat in the grasped target of treatment. Consequently, even if the target is hard like a calculus, treatment such as breaking can be carried out efficiently.

Figure 11A:
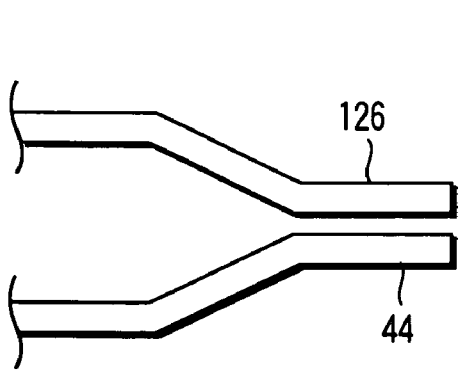
FIG. 11A is an explanatory view showing a first modification of a distal end treatment portion and a holding portion of the ultrasonic treatment apparatus of the fourth embodiment.
Figure 11B:
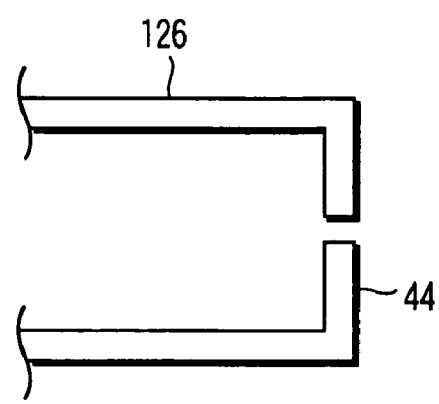
FIG. 11B is an explanatory view showing a second modification of the distal end treatment portion and the holding portion of the ultrasonic treatment apparatus of the fourth embodiment.

FIGS. 11A and 11B show first and second modifications of the distal end treatment portion 44 and the grasp portion 126 of the fourth embodiment. The distal end treatment portion 44 and the grasp portion 126 may have any shapes other than these modifications, as far as they can grasp a target of treatment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic treatment apparatus for treating a treated part, said ultrasonic treatment apparatus comprising:
    an endoscope comprising an insertion portion to be inserted into a body cavity, said insertion portion having a distal end portion and a rear end portion positioned at the endoscope, said insertion portion operable to provide visibility of the treated part to the endoscope;
    a treatment unit having an ultrasonic vibrator operable to generate ultrasonic vibrations;
    a treatment portion operable to perform treatment by utilizing the ultrasonic vibrations generated by the ultrasonic vibrator;
    an ultrasonic driver operable to transmit an electric signal to control the ultrasonic vibrator;
    a treatment unit holding portion connected to an exterior of the distal end portion of the insertion portion and comprising the treatment unit;
    a cable connected to a proximal end of the treatment unit and directly connecting the treatment unit to the ultrasonic driver to transmit the electric signal to the ultrasonic vibrator, said cable comprising a distal end; and
    at least one bundle member configured to removably receive the insertion portion and the cable,
    wherein the cable extends outside the insertion portion along the insertion portion, and said treatment unit holding portion is configured to receive the distal end of the insertion portion and the distal end of the cable.

2. The ultrasonic treatment apparatus according to claim 1, wherein the treatment unit holding portion has a vibrator hole, and the ultrasonic vibrator is sealed within the vibrator hole.

3. The ultrasonic treatment apparatus according to claim 1, wherein the treatment unit holding portion is fixed to a node position of the ultrasonic vibrations of the treatment unit.

4. The ultrasonic treatment apparatus according to claim 3, wherein the treatment portion has a distal end portion located at a position a quarter wavelength of the ultrasonic vibrations of the treatment unit apart from the node position.

5. The ultrasonic treatment apparatus according to claim 1, further comprising:
    another treatment unit attached to the treatment unit holding portion and having another ultrasonic vibrator which generates ultrasonic vibrations, and another treatment portion which grasps a target of treatment in cooperation with the treatment portion and performs treatment by utilizing the ultrasonic vibrations generated by the other ultrasonic vibrator;
    another cable which transmits an electric signal to the other ultrasonic vibrator and is bundled together with the cable and the insertion portion by the at least one bundle member; and
    an ultrasonic oscillating apparatus to which the cable and the other cable is connected and drives the ultrasonic vibrator and the other ultrasonic vibrator in phases opposite to each other.

6. The ultrasonic treatment apparatus according to claim 5, wherein the ultrasonic vibrator and the other ultrasonic vibrator are driven at frequencies different from each other.

7. The ultrasonic treatment apparatus according to claim 1, wherein the cable connects the ultrasonic driver with the treatment unit holding portion without passing through the endoscope.

* * * * *